United States Patent
Taniguchi et al.

(10) Patent No.: US 9,517,057 B2
(45) Date of Patent: Dec. 13, 2016

(54) SHAFT OF A LAPAROSCOPIC INSTRUMENT

(75) Inventors: Kazunori Taniguchi, Hamburg (DE); Sebastian Kracht, Hamburg (DE); Thomas Aue, Wedel (DE); Dennis Bernhardt, Hamburg (DE); Harald Hanke, Hamburg (DE); Simon Hirschfeld, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 274 days.

(21) Appl. No.: 14/239,101

(22) PCT Filed: Jul. 26, 2012

(86) PCT No.: PCT/EP2012/003176
§ 371 (c)(1),
(2), (4) Date: Feb. 14, 2014

(87) PCT Pub. No.: WO2013/023740
PCT Pub. Date: Feb. 21, 2013

(65) Prior Publication Data
US 2014/0236131 A1     Aug. 21, 2014

(30) Foreign Application Priority Data
Aug. 15, 2011   (DE) .................. 10 2011 110 136

(51) Int. Cl.
  *A61B 17/00* (2006.01)
  *A61B 17/29* (2006.01)
  *A61B 18/14* (2006.01)

(52) U.S. Cl.
  CPC ......... *A61B 17/00234* (2013.01); *A61B 17/29* (2013.01); *A61B 18/1445* (2013.01);
(Continued)

(58) Field of Classification Search
  CPC .................. A61B 17/00234; A61B 2017/2901
  See application file for complete search history.

(56) References Cited

U.S. PATENT DOCUMENTS

| | | | | |
|---|---|---|---|---|
| 4,507,356 A | * | 3/1985 | Watabe | B32B 27/08 428/315.5 |
| 4,753,840 A | * | 6/1988 | Van Gompel | B32B 27/12 428/171 |

(Continued)

FOREIGN PATENT DOCUMENTS

| | | | |
|---|---|---|---|
| DE | EP 1044656 A1 * | 10/2000 | ............. A61C 1/148 |
| DE | 103 41 984 B3 | 6/2005 | |

(Continued)

OTHER PUBLICATIONS

Feb. 27, 2014 International Preliminary Report on Patentability issued in International Patent Application No. PCT/EP2012/003176.

(Continued)

*Primary Examiner* — Lynsey Crandall
*Assistant Examiner* — Amanda Steinberg
(74) *Attorney, Agent, or Firm* — Oliff PLC

(57) ABSTRACT

A shaft of a laparoscopic instrument, having a ceramic tube which extends over the main length of the shaft and has a sheath which encloses the ceramic tube in at least some regions, is situated to cover those regions of the ceramic tube that are at risk of breakage and is designed to prevent the splinters of ceramic from penetrating through the sheath. The ceramic tube forms a predetermined breaking point in the region of the sheath.

13 Claims, 4 Drawing Sheets

(52) U.S. Cl.
CPC ............... *A61B 2017/0088* (2013.01); *A61B 2017/00238* (2013.01); *A61B 2017/2901* (2013.01); *A61B 2090/037* (2016.02)

(56) References Cited

U.S. PATENT DOCUMENTS

| | | |
|---|---|---|
| 5,257,999 A | 11/1993 | Slanetz, Jr. |
| 5,389,104 A | 2/1995 | Hahnen et al. |
| 2005/0209618 A1* | 9/2005 | Auld .................. A61F 9/00 606/166 |
| 2008/0300611 A1 | 12/2008 | Houser et al. |

FOREIGN PATENT DOCUMENTS

| | | |
|---|---|---|
| DE | 10 2004 020383 A1 | 11/2005 |
| JP | 2009-018160 A | 1/2009 |
| WO | WO 95/03741 A2 | 2/1995 |
| WO | WO 97/47249 A1 | 12/1997 |
| WO | WO 2005/086772 A2 | 9/2005 |
| WO | 2008-150650 A1 | 12/2008 |

OTHER PUBLICATIONS

Translation of Feb. 27, 2014 Written Opinion of the International Searching Authority issued in International Patent Application No. PCT/EP2012/003176.

Oct. 24, 2012 Search Report issued in International Patent Application No. PCT/EP2012/003176 (with translation).

\* cited by examiner

SHAFT OF A LAPAROSCOPIC INSTRUMENT

RELATED FIELD

The disclosure relates to the shaft of a laparoscopic instrument.

BACKGROUND

Laparoscopic instruments having a tungsten carbide shaft have recently been discussed. The advantage of ceramics in comparison with steel, which is generally, used is that ceramics have a much greater strength, in particular a better flexural rigidity, which is a major advantage in laparoscopic instruments having a long, thin shaft, when greater forces are exerted with such instruments.

However, the danger of breakage is a disadvantage in the case of shafts made of ceramic. If the load limits are exceeded, the shaft does not bend, as would be the case with a shaft made of steel, but it breaks instead. However, this could have catastrophic consequences in an operation with such an instrument. If a ceramic shaft breaks, sharp fracture edges are usually formed and could lead to injuries in the patients body. Furthermore, splinters may be formed and can lead to serious problems if they enter the abdominal cavity, especially since such splinters are difficult to locate.

If the ceramic is enclosed by a sheath which covers at least those regions of the ceramic tube that are at risk of breakage. The sheath is also designed with material properties such that it prevents the penetration of broken ceramics; although it does not prevent the ceramic from breaking, the harmful consequences of such a break are prevented. Sharp edges that are formed on the ceramic tube in the event of breakage cannot penetrate through the enclosing sheath. The surrounding body tissue is thus prevented from coming in contact with sharp edges. The resulting ceramic splinters remain inside the sheath and cannot be lost. Thus, on the whole, this yields an instrument that makes use of the high rigidity of the ceramic tube without having to accept its risks.

US 2005/0209618 A1 discloses a ceramic rod sheathed by an elastic tube, and US 2008/0300611 A1 discloses a metal-sheathed ceramic rod. Both of these designs reduce the harmful consequences of breaking ceramics due to a sheath which covers the breakage.

However, with the known designs, the ceramic rod extends essentially uniformly and with constant strength values over the length of the shaft. If an excessive load is applied to the ceramic, it may break at any location although its position cannot be predicted.

A laparoscopic instrument having a predetermined breaking point on a member that transmits a force is known per se from U.S. Pat. No. 5,389,104 A.

SUMMARY

The object of the present application is to design a generic shaft having breaking properties that are more controllable.

This object is achieved with the features of a characterizing part.

With the present application, the ceramic tube has a predetermined breaking point, which will break due to an overload and thereby defines the breaking point at the predetermined location of the predetermined breaking point. It is thus possible to shift the break to a location where it will be less problematical.

The predetermined breaking point may be formed by any weakness in the ceramic tube. According to some embodiments, the predetermined breaking point may advantageously be embodied as a groove-shaped weakened location in the ceramic tube.

Alternatively, the predetermined breaking point may also be formed without weakening of the ceramic tube. In this case, the ceramic tube is weakened indirectly because the support provided by the reinforcing tube is omitted at the predetermined breaking point.

In some embodiments, the sheath is preferably formed at a radial distance from the predetermined breaking point, so it creates a space from it, where ceramic splinters are able to move out of the way in the event of a break without acting directly on the sheath.

The predetermined breaking point may be located in a suitable position on the shaft, where a break would not be very problematical. According to some embodiments, the predetermined breaking point is advantageously adjacent to an end holder of the shaft. A break thus occurs near the end holder. The end holder is usually located on the proximal end of the shaft and always remains outside of the body, so a break is less dangerous. Furthermore, with this arrangement, the predetermined breaking point is located near the end holder in a region where the risk of a break is higher for static reasons anyway.

The sheath enclosing the ceramic tube may be made of various suitable materials. For example, a sufficiently strong plastic may be used. However, a sheath is preferably formed by a metal tube, which provides especially effective protection against penetrating edges or splinters of ceramics and has the advantages of having a reinforcing effect and being manufacturable in the usual technology of medical precision mechanics.

The connection to the ceramic tube is a problem in the case of a sheath consisting of a metal tube. Adhesions are not favored in medical technology. Other types of connections, e.g., screw connections, are more complex. In some embodiments, the metal tube has internal flanges on the ends between which the ceramic tube is held. Therefore, direct connections between the metal tube and the ceramic tube are not necessary. The ceramic tube lies loosely in a form-fitting frame between the internal flanges and inside the metal tube on the outside. It is only necessary to secure at least one of the two internal flanges after inserting the ceramic tube. The internal flange may advantageously be made of metal and can be connected to the metal tube effectively in an extremely simple manner, e.g., by a spot weld, by clamping or the like.

Alternatively, the sheath may advantageously be designed as a cloth. Cloth of a suitable strength is available in a variety of forms, for example, in the form of metal cloth, glass cloth or the like. It may be formed as a cloth tube arranged around the sheath to thereby prevent the penetration of sharp ceramic edges or ceramic splinters. It is possible to create especially simple, inexpensive designs in this way.

The cloth may be advantageously embedded in a plastic matrix. A cloth tube is formed, having especially good manufacturing properties and use properties with the plastic matrix, for example, with regard to its dimensional stability.

The sheath may preferably consist of a flexible material in at least some areas, this material being formed as a cast material or as an adhesive and thus being applicable to the site. It is thus possible for example to provide for locations of a difficult design, where the flexible material is excellently suited for protection against splinters.

An envelope is advantageously also provided around this material, to impart additional strength to the flexible material and in particular to optionally also serve as a casting mold to facilitate production.

The sheath may advantageously extend over the entire length of the ceramic tube to be able to cover breaks, regardless of where they occur in the ceramic tube.

Ceramics that are suitable for strength reasons are usually poor electric conductors, like most ceramics. However, an electrically conductive ceramic is preferably used. This has the advantage that the ceramic tube, as is known of instruments with metal tubes, can be used as an inlet line for transmitting electric current from the proximal end of the instrument to its distal end. An insulating cover serves to provide external insulation to prevent unwanted application of current to the body tissue.

The ceramic tube is preferably made of tungsten carbide. Tungsten carbide is characterized by a particularly high strength and a good electric conductivity.

BRIEF DESCRIPTION OF THE DRAWINGS

The embodiments of the disclosure are diagramed schematically as examples in the drawings, in which.

DETAILED DESCRIPTION

Figure 1:
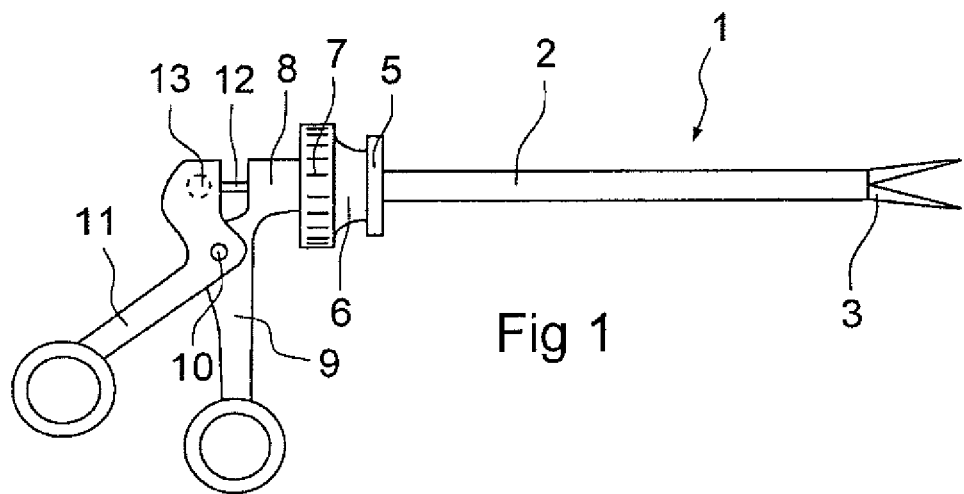
FIG. 1 shows the side view of an embodiment of the laparoscopic instrument having an elongated shaft.

FIG. 1 shows a side view of a laparoscopic instrument 1 in the form of shaft tongs having an elongated shaft 2, on whose distal end an end effector in the form of a tong jaw 3 is arranged; it may also be formed as scissors jaws.

The shaft 2 is attached at its proximal end area to an end holder formed as a disk 5, serving as identification by color coding, for example, and being attached to a rotating ring 6 that has external flanging 7 and is supported rotatably on a main body 8 in this exemplary embodiment.

The main body 8 is part of a handle with a fixed handle piece 9 attached to the main body 8 and a movable handle piece 11 pivotably connected to a joint 10 opposite the former. The two handle pieces 9, 11 are each provided with a finger grip ring, shown in FIG. 1.

The shaft 2 has a tubular shape with an operating rod 12 passing through it, said operating rod being supported in an articulated fashion at 13 in the movable handle piece 11 and thus being moved in the axial direction of the shaft 2 with a movement of the handle pieces 9, 11 opposite one another. The distal end of the operating rod 12 is coupled to the jaws 3 in a manner not shown here, to open or close the jaws by a movement of the operating rod 12.

By turning the rotating ring 6 with respect to the main body 8, the jaws 3 and the shaft 2 attached to the rotating ring 6 are entrained in the rotational movement. The opening plane of the jaws 3 can be rotated into the desired position in this way. This rotatability may also be omitted in a simplified instrument. Manual operation of the handle using the handle pieces 9 and 11 may also have a different design, e.g., in the form of an in-line handle.

For reasons of simplicity of the diagram in FIG. 1, the shaft 2 is shown as relatively short and thick. However, for laparoscopic use, it may be extremely long and thin, e.g., with a diameter of only a few millimeters and a length of several decimeters.

The instrument 1 shown here is usually inserted through a laparoscopic port into the abdominal cavity of a patient in a laparoscopic operation to perform procedures there. The instrument 1 shown in FIG. 1 may be designed as tongs or as scissors but may also have a stationary blade on its distal end.

The instrument 1 is designed for high-frequency surgery in particular, so it has at least one electrode on its distal end area. For example, one of the two branches of the jaws 3 may be designed as an electrode. Then the distal electrode must be connected to corresponding electrical lines to the proximal region of the instrument 1 over the length of the shaft 2 in order to be able to connect it there to a high-frequency generator by means of a suitable cable connection, for example.

When using the instrument 1 in the body, it is frequently also used as a lever, for example, to force a body organ out of the way. Substantial bending forces then occur occasionally, resulting in an overload on the shaft 2. If this shaft consists essentially of a conventional metal tube, it becomes bent in such due to overload and is thus rendered unusable for further use, in particular because a bent or kinked shaft can no longer be moved through the tubular sheath of a laparoscopic port.

Figure 2:
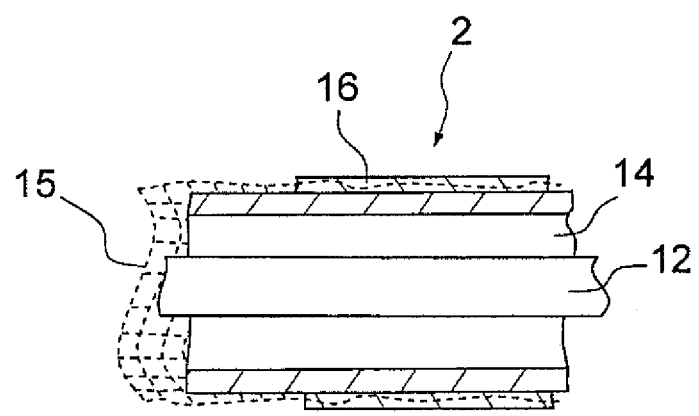
FIGS. 2-8 show partial pieces of the shaft cut in the longitudinal direction in different embodiments.

A ceramic tube 14 is used to increase the load limit value at which the instrument 1 becomes useless and is an essential part of the shaft 2, imparting its flexural strength to the shaft. FIG. 2 shows a region of the shaft 2 in a longitudinal section. This shows the ceramic tube 14, which encloses the operating rod 12.

Higher strength values can be achieved in the design according to FIG. 2 because ceramic is superior to a metal tube with regard to the flexural rigidity. However, the stiffer ceramic may also be overloaded. The ceramic tube 14 would then break. The sharp breaking edges and ceramic splinters that are customary in breakage of ceramics then occur. If these enter or come in contact with the patient's body, they result in injuries.

To prevent this, the ceramic tube 14 is enclosed by a sheath.

In the specific embodiment of FIG. 2, the sheath is designed as cloth tubing 15 enclosing the ceramic tube 14. It may be a bare cloth tubing enclosing the ceramic tube 14 loosely, as shown at the left in FIG. 2 or as shown at the right in FIG. 2, the cloth tubing 15 may also be cast in a plastic matrix 16 which imparts an advantageous fit in assembly to the cloth tubing 15 and improves its handleability. Furthermore, this also prevents the extremely fine ceramic splinters from penetrating through the cloth mesh.

As already mentioned, in the case of an instrument intended for electrosurgery, with one or more electrodes in the distal end region, electric lines are required between the distal and proximal end regions of the shaft 2. In the case of the instrument in FIG. 2, the ceramic tube 14 may be designed to be electrically conducting and may be used as a line for these purposes.

It is particularly suitable to form the ceramic tube 14 of tungsten carbide which combines especially good strength properties with good electrical conductivity. In this case, as is known for metal shafts, the ceramic tube 14 is to be insulated electrically with respect to the outside. This can be accomplished by the plastic matrix 16. Otherwise it is also possible to provide an additional insulation layer.

Figure 3:
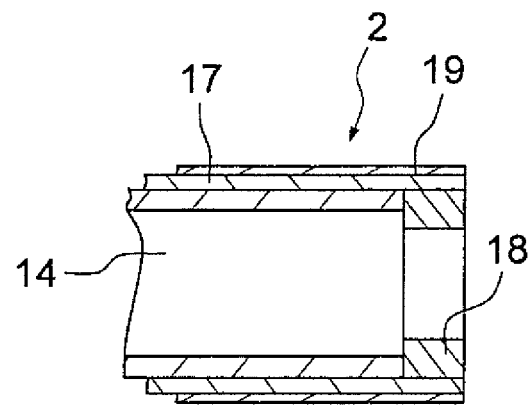

FIG. 3 shows another embodiment of the shaft 2, again with the ceramic tube 14 preferably made of tungsten carbide and again enclosed by a sheath to protect against breakage and splinters. However, in the exemplary embodiment of FIG. 3, this sheath is embodied as a metal tube 17 enclosing the ceramic tube 14 with a tight fit in the exemplary embodiment shown here.

However, the fastening between the ceramic tube 14 and the metal tube 17, which is required for secure assembly, proves to be difficult as adhesives are not desirable with medical instruments. The design illustrated in FIG. 3 seeks to remedy this situation with an internal flange 18 situated in the end area of the metal tube 17. A corresponding internal flange is also applied to the other end region of the metal tube 17. The ceramic tube 14 is therefore held securely in the axial direction at both ends of the shaft 2. Any additional means of fastening it to the metal tube 17 may be omitted.

In assembly, the inside flange 18 is initially omitted at one end of the metal tube 17 and the ceramic tube 14 can be inserted from this end. Then an internal flange is inserted at this end and connected to the metal tube 17. The internal flange 18 may be made of metal in a suitable manner and connected to the metal tube 17 by a spot weld, for example. However, other possibilities may also be utilized in fastening the internal flange 18, such as threaded screw connections and the like, for example.

In the embodiment according to FIG. 3, the metal tube 17 is outside of the ceramic tube 14 and is electrically conductive. If it is used as a current conductor, external insulation is necessary. An insulating coating 19 of a suitable material may be provided for this purpose.

In the embodiments according to FIGS. 2 and 3, the ceramic tube 14 is covered on the outside by a sheath 15, 16 and/or 17, to protect the patient's body from fragments of the ceramic tube 14 in each case. These fragments may occur at any location on the shaft 2. The covering sheath must therefore extend over the entire length of the ceramic tube 14.

In the embodiments of the instrument shaft described above, the ceramic tube 14, which is at risk of fracturing is always formed uniformly over its entire length, as is the metal tube 17. If the ceramic tube 14 breaks, then it is impossible to predict where this will occur. To prevent this, a predetermined breaking point is provided, allowing the break to occur at a predetermined location where it is less problematical.

Figure 4:
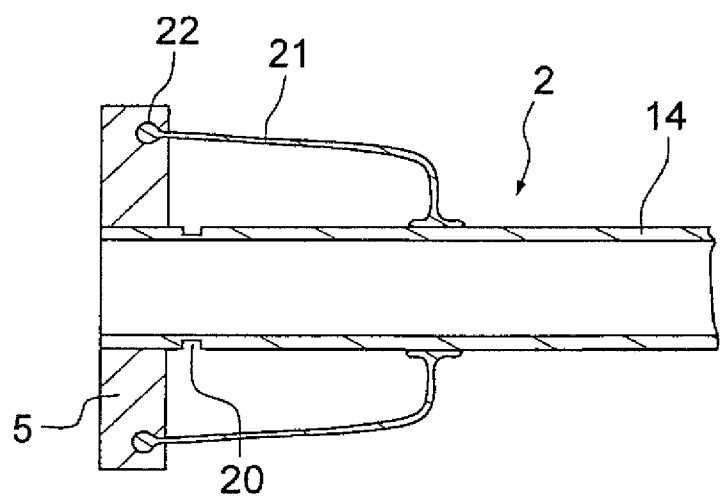

FIG. 4 shows one embodiment of the shaft 2 in which the ceramic tube 14 is provided with a predetermined breaking point in its end area connected to the disk 5, this predetermined breaking point being formed, for example, in the form of the outer annular groove 20 shown here.

The predetermined breaking point with the annular groove 20 is situated in a particularly suitable location, as shown in FIG. 4, namely in the proximal end region of the shaft 2, where there is a greater risk of breakage anyway in the usual handling of the instrument 1, and this region is usually outside of the patient's body on which the procedure is to be performed. Therefore, if the ceramic tube 14 of the design shown in FIG. 4 breaks, there is a high probability that this will occur at the predetermined breaking point formed by the annular groove 20.

It is thus sufficient to enclose only the region of the annular groove 20 with a sheath, this sheath being formed according to FIG. 4 as a protective cap 21, which encloses the ceramic tube 14 at a distance and is attached in a form-fitting manner at its one edge in the groove 22 shown in FIG. 4 in the disk 5 and encloses the ceramic tube 14 in an annular form at its other edge. The protective cap 21 may be made of a stable plastic material, for example, or may also be made of the cloth material used as a sheath according to FIG. 2, for example.

The radial distance at which the protective cap 21 encloses the ceramic tube 14 in the region of the annular groove 20 can allow lateral yielding of the breaking points in the event of breakage at the annular groove 20, without any damage to the protective cap 21, and may also receive any splinters that are formed in a break in the interior space.

The design of the protective cap 21 with a radial distance from the ceramic tube 14 ensures a relatively large outside diameter of the shaft 2 in the region of the safety cap 21. At this location, however, namely in the proximal end region of the shaft 2, this does not cause interference because this end region of the shaft 2 always remains outside of the body in laparoscopic procedures.

Figure 5:
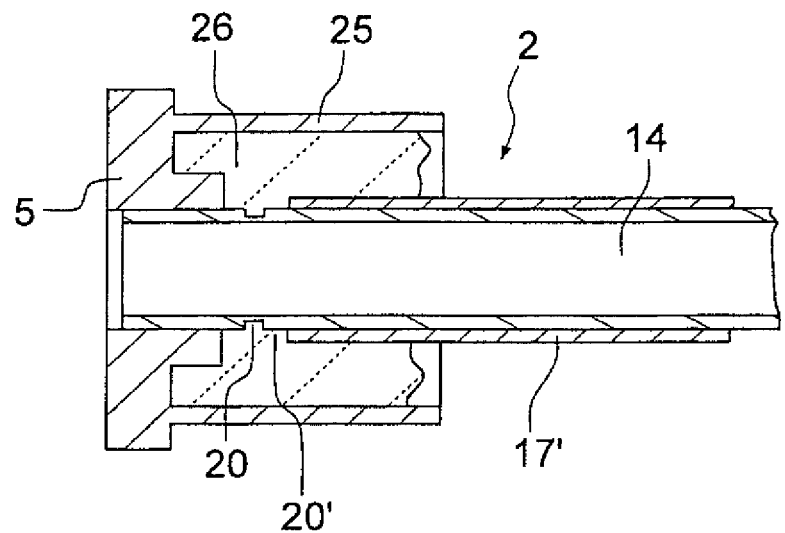

FIG. 5 shows an embodiment of the shaft which resembles the design of FIG. 4. Instead of the protective cap 21, an envelope 25 is provided here; for the sake of simplicity, this envelope is made of metal, for example, formed as an integral part with the disk 5 forming the end holder of the shaft 2. The envelope 25 encloses the end region of the shaft 2 adjacent to the disk 5 and encloses the region of the predetermined breaking point formed by the annular groove 20. The interior of the envelope 25 is filled with a casting compound 26, which may be in the form of a castable material, an adhesive material or the like and encloses the shaft 2 in the region of the predetermined breaking point 20 in a permanently elastic manner after the cast material has set up, for example. The envelope 25 may then be used as a casting mold.

FIG. 5 shows that outside of the predetermined breaking point, the ceramic tube 14 is enclosed with a reinforcing tube 17' made of metal, for example. Instead of metal, another suitable material may also be used for the reinforcing tube 17'.

The reinforcing tube 17' provides additional rigidity for the ceramic tube 14. The reinforcing tube 17' has a gap 20', which also serves as a predetermined breaking point in the region of the predetermined breaking point 20. Therefore this results in an additional weakening of the shaft 2 in the area of the predetermined breaking point.

Figure 6:
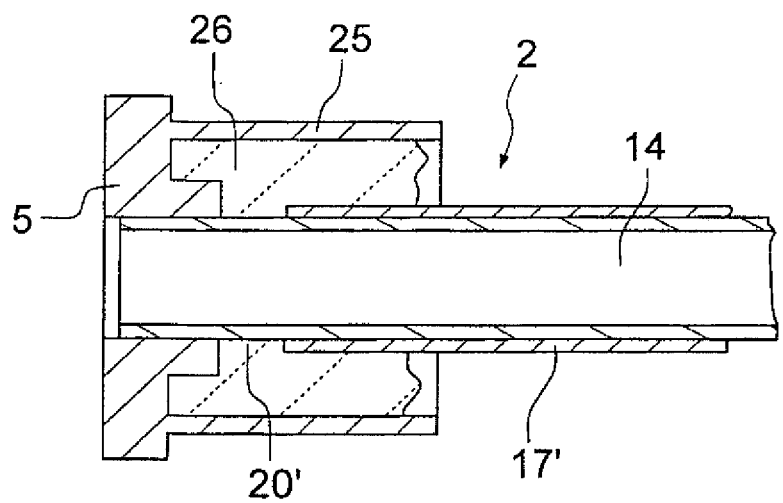

In a variant of this, FIG. 6 shows that the annular groove 20 may also be omitted in the region of the gap 20'. Only the gap 20' in the reinforcing tube 17' is sufficient at this point to define the predetermined breaking point.

Figure 7:
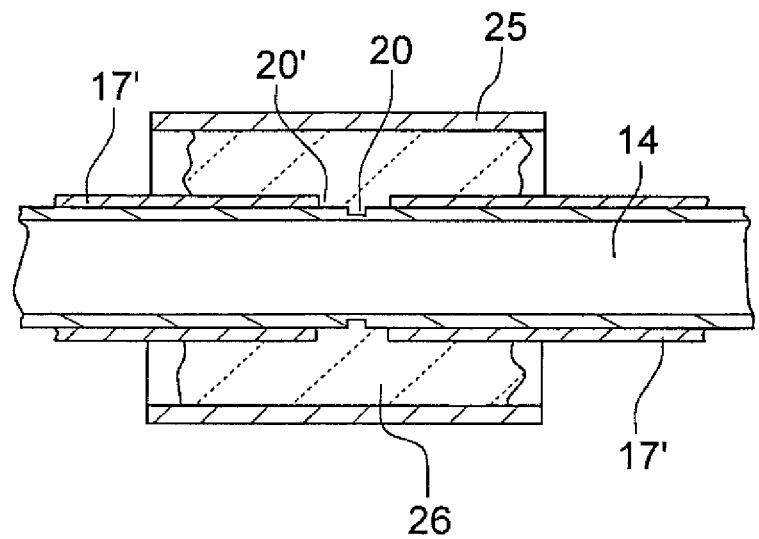

FIG. 7 shows a variant of the embodiment of FIG. 5 in which the predetermined breaking point is situated not in the vicinity of the end holder, i.e., near the disk 5 but instead is situated at another location on the shaft 2. Here again, as in the design according to FIG. 5, the predetermined breaking point is formed as a gap 20' in the reinforcing tube 17' and in addition is also formed as a weakened annular groove 20 in the ceramic tube 14.

Figure 8:
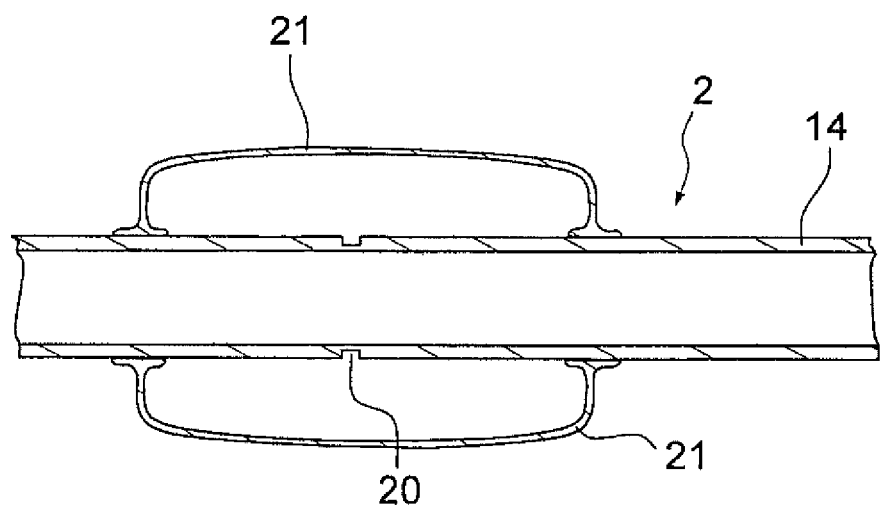

FIG. 8 shows a corresponding embodiment variant of the design according to FIG. 4, in which a corresponding design is again situated on the ceramic tube 14 at a distance from the disk 5.

With the designs according to FIGS. 4 and 5, the predetermined breaking point may also be formed by a gap in a reinforcing tube 17' enclosing the ceramic tube 14 instead of being formed by an annular groove 20 in the ceramic tube 14. Likewise the reinforcing tube 17' may be omitted from the design according to FIG. 7.

The invention claimed is:

1. A shaft of a laparoscopic instrument, the shaft comprising:
   a ceramic tube including a predetermined breaking point formed in the ceramic tube; and a sheath enclosing: (i) the ceramic tube in at least one region of a plurality of regions of the ceramic tube that is at risk of breakage, and (ii) the predetermined breaking point formed in the ceramic tube, the sheath being spaced apart from the ceramic tube by a radial distance, wherein
upon breakage of the ceramic tube, the sheath is configured to prevent splinters of ceramic material caused by the breakage from penetrating through the sheath.

2. The shaft according to claim 1, wherein the predetermined breaking point is formed as a groove in the ceramic tube.

3. The shaft according to claim 1, wherein the ceramic tube is provided with an applied reinforcing tube, and the predetermined breaking point is formed as a gap in the reinforcing tube.

4. The shaft according to claim 1, wherein the predetermined breaking point is situated at an end region of the shaft that is connected to an end holder.

5. The shaft according to claim 1, wherein the sheath is formed as a metal tube.

6. The shaft according to claim 5, wherein the metal tube is connected to internal flanges at ends between which the ceramic tube is held.

7. The shaft according to claim 1, wherein the sheath is formed as a cloth.

8. The shaft according to claim 7, wherein the cloth is embedded in a plastic matrix.

9. The shaft according to claim 1, wherein the sheath is formed as a casting material or as an adhesive material.

10. The shaft according to claim 9, wherein the casting material or the adhesive material is enclosed by an envelope.

11. The shaft according to claim 1, wherein the sheath extends over an entire length of the ceramic tube.

12. The shaft according to claim 1, wherein the ceramic tube is formed from an electrically conducting ceramic and is provided with an outer insulating coating.

13. The shaft according to claim 12, wherein the ceramic tube is formed from tungsten carbide.

* * * * *